United States Patent [19]
Moore

[11] Patent Number: 4,567,900
[45] Date of Patent: Feb. 4, 1986

[54] INTERNAL DEPLOYABLE DEFIBRILLATOR ELECTRODE

[76] Inventor: J. Paul Moore, 1343 Belmont Ave., Youngstown, Ohio 44504

[21] Appl. No.: 617,017

[22] Filed: Jun. 4, 1984

[51] Int. Cl.[4] .............................................. A61N 1/04
[52] U.S. Cl. .................................. 128/784; 128/419 D
[58] Field of Search ............... 128/419 D, 419 P, 784, 128/785

[56] References Cited

U.S. PATENT DOCUMENTS

| 2,985,172 | 5/1961 | Timm et al. | 128/784 |
| 3,646,940 | 3/1972 | Jones | 128/784 |
| 3,844,292 | 10/1974 | Borduc | 128/419 P |
| 4,291,707 | 9/1981 | Heilmon et al. | 128/784 |
| 4,424,818 | 1/1984 | Dooring et al. | 128/784 |

FOREIGN PATENT DOCUMENTS 095726 7/1983 European Pat. Off. ......... 128/419 D

OTHER PUBLICATIONS

Berens et al. "American Journal of Cardiology", vol. 34, Sep. 1974, pp. 325-332.

Primary Examiner—William E. Kamm
Attorney, Agent, or Firm—Harpman & Harpman

[57] ABSTRACT

An internally deployable resilient continuous electrode assembly for placement through a catheter comprises a distortable electric conductor movable through the catheter in a first position and deployable therefrom in a second position onto the epicardial surface of the heart without the need of a general anesthetic and minimizing the risk for the patient. The distortable electric conductor has a plurality of distortable flat conductor strips conductively connected at their ends to the distortable electric conductor so as to provide an enlarged surface area of contact with the heart for defibrillating episodes.

1 Claim, 6 Drawing Figures

U.S. Patent  Feb. 4, 1986  4,567,900
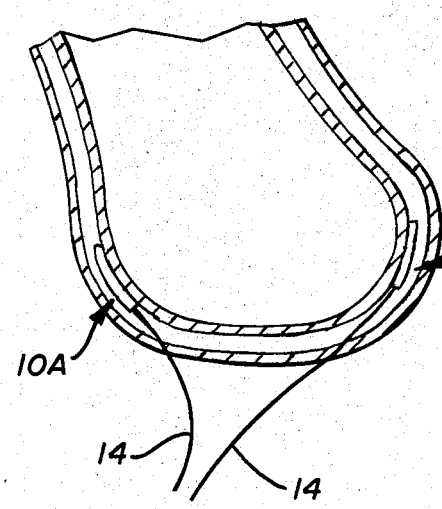
FIG. 1
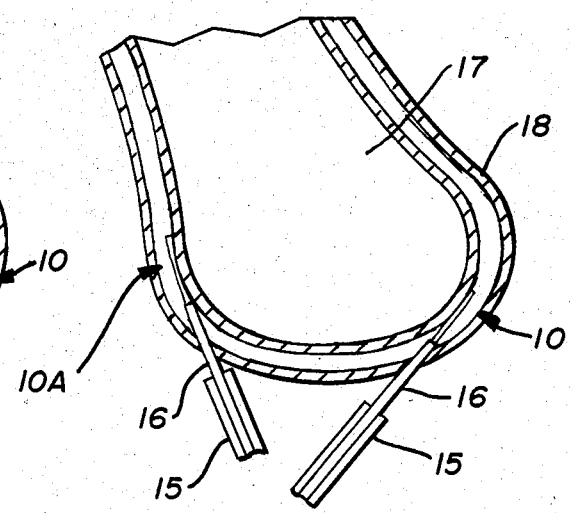
FIG. 2
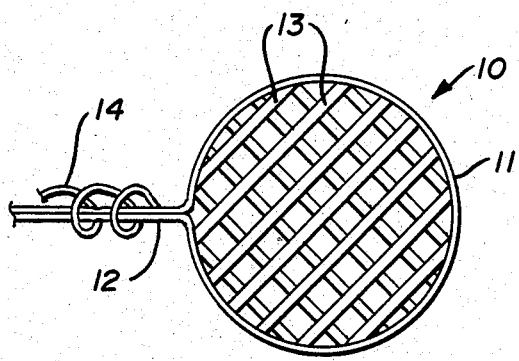
FIG. 3
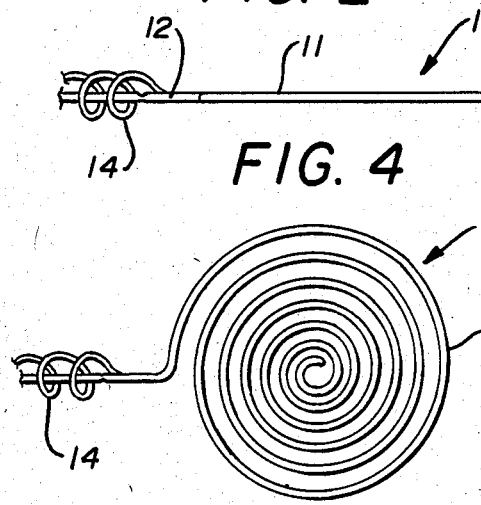
FIG. 4
FIG. 5
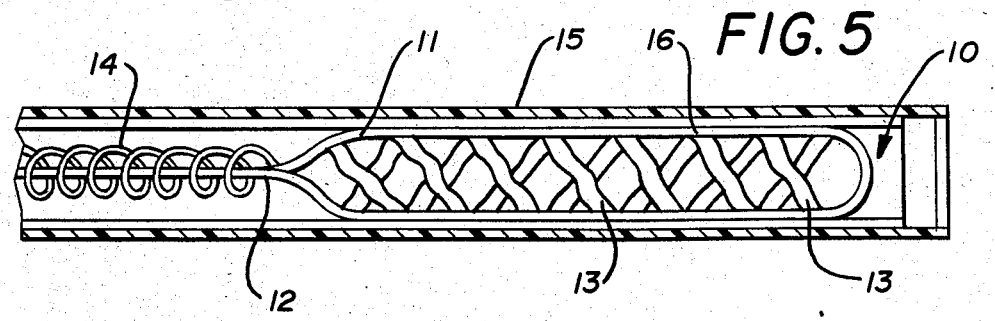
FIG. 6

INTERNAL DEPLOYABLE DEFIBRILLATOR ELECTRODE

BACKGROUND OF THE INVENTION

1. Technical Field

This invention relates to implantable defibrillators that have been developed to sense and control ventricular fibrillation which if not treated promptly would lead to sudden death.

2. Description of the Prior Art

Prior art implantable defibrillators are presently used in patients that have had an episode of ventricular fibrillation or hemodynamically unstable ventricular tachycardia.

Prior art implantable defibrillators consist of a pulse charge generator and a pair of electrodes, one of which is incorporated into an intravascular catheter placed in the superior vena cava at the level of the right atrial junction. The other electrode takes the form of a rectangular patch that covers the apex of the heart. The electrode also acts as a sensor to detect the onset of ventricular tachyarrhythmias.

Other prior art devices have shown the introduction of electrodes into the heart for pacing and monitoring the same. See for example U.S. Pat. Nos. 4,289,138 and 3,865,118.

In U.S. Pat. No. 4,289,138 an electrode assembly is shown for use with a catheter to be implanted within the heart. The electrodes are formed on the free ends of wires of different lengths rather than the prior known closed loop.

U.S. Pat. No. 3,865,118 discloses a transvenous coaxial catheter which is passed through a single channel to the heart. The catheter provides at least two insulated spacially adjustable electrical conductors. The device is used to pace the heart.

Applicant's device utilizes prior art implantable defibrillator pulse charge generator and detection technology present available with a new and novel internally deployed collapsible electrode patch that can be positioned on the epicardial surface by maneuvering a catheter through the chest wall to the heart and deploying the collapsed electrode, which on deployment regains its original shape.

SUMMARY OF THE INVENTION

An internally deployable defibrillator electrode is for use with an implantable defibrillator which monitors and detects an episode of ventricular fibrillation and automatically supplies an electric pulse discharge to the heart through the electrodes. The internally deployed defibrillation electrode consists of a collapsible patch that is deployed through a catheter inserted through the chest wall of the patient. The electrode patch is positioned on the epicardial surface regaining its original characteristics once deployed from the catheter. Typically, a pair of electrode patches are positioned appropriately on the heart to provide the required electrode surface area for adequate electrical discharge.

DESCRIPTION OF THE DRAWINGS

FIG. 1 is a front plan view of a portion of a heart with a pair of electrode patches positioned thereon;

FIG. 2 is a front plan view of a portion of the heart showing the deployment of the electrode patches through catheters;

FIG. 3 is an enlarged top plan view of a collapsed electrode patch;

FIG. 4 is a side elevation of the electrode patch of FIG. 3;

FIG. 5 is a top plan view of an alternate form of the electrode patch and;

FIG. 6 is a cross sectional view of a catheter and collapsed electrode patch ready for deployment.

DESCRIPTION OF THE PREFERRED EMBODIMENT

An internally deployable defibrillation electrode 10 can be seen in FIGS. 3, 4 and 6 of the drawings comprising a spring wire loop 11 extending integrally from a bifurcated guide wire 12. The spring wire loop 11 is preformed to retain its loop configuration after deformation by compression as is well known in the medical technical field. A multiplicity of conductive foilized flat strips 13 extend transversely between and are conductively secured to opposite disposed points on the spring wire loop 11 in a crisscross pattern. The foilized flat strips 13 can be made from any one of a variety of materials having the desired thickness, flexibility and conductive nature required.

The overlapping foilized flat strips 13 are evenly spaced in relation to one another to form a contour conforming conductive surface that is of a substantial surface area required to provide an adequate discharge rate produced by a defibrillator, not shown.

An insulated wire lead 14 extends from a portion of the guide wire 12 adjacent the spring wire loop 11 supplying electrical current thereto during pulse discharge from the defibrillator at the onset of an episode of ventricular fibrillation or hemodynamically unstable ventricular tachycardia occurrences.

Referring now to FIG. 3 of the drawings, an end portion of a delivery catheter 15 can be seen which is well known in the art and used to provide a conduit into the patient's body for a variey of medical procedures. A deployment catheter 16 is movably positioned within said delivery catheter 15 which acts as a delivery guide within the patient. The internally deployable defibrillator electrode 10 is collapsed and positioned within the deployment catheter 16 in an elongated manner with the guide wire 12 and insulated wire lead 14 trailing outwardly therefrom.

It will be evident from the above description that the flexibility and arrangement of the foilized strips 13 will be such that they will readily bend and fold as the spring wire loop 11 is collapsed within the deployment catheter 16 and yet fully expand into their precollapsed position as seen in FIG. 3 of the drawings as the spring wire loop 11 expands and reassumes its loop shape as it moves outwardly from the deployment catheter when the same is properly positioned adjacent to the heart.

Referring now to FIGS. 1 and 2 of the drawings, a placement diagram of a heart 17 can be seen within its pericardial sac 18. In FIG. 2 of the drawings, the placement procedure is shown wherein the delivery catheter 15 acting as a guide has been positioned within the patient with the deployment catheter 16 extending outwardly therefrom. The internal deployable defibrillator electrode 10 is then deployed therefrom in its collapsed state and immediately regains its loop configuration as hereinbefore described on the epicardial surface. The placement procedure is repeated so that a second internally deployable defibrillator electrode 10A can be properly placed on the other side of the heart 17.

Referring now to FIG. 1 of the drawings, the completed placement of both the internally deployed defibrillator electrodes 10 and 10A with the lead wires 14 extending therefrom has been accomplished. The lead wires 14 are conductively connected to the defibrillator in a manner that is well known and understood by those skilled in the art as will be the surgical procedure utilizing a delivery catheter.

Referring now to FIG. 5 of the drawings, an internally deployable defibrillator electrode 19 in an alternate form can be seen wherein a flattened coil configuration 20 of the spring wire loop 11 is utilized without foilized strips to provide the adequate surface area for the proper pulse discharge as heretofore described.

It will also be apparent that the exact placement of the internally deployable defibrillator electrodes 10 and 10A and the defibrillator is generally the same as is now practiced with the surgically implanted defibrillator devices without the need of a general anesthetic which is presently required due to the size and nature of the electrode patch presently available.

It will thus be seen that a new and novel deployable defibrillator electrode has been illustrated and described and that it will be obvious to those skilled in the art that various changes and modifications may be made therein without departing from the spirit of the invention and having thus described my invention what I claim is:

1. In an internally deployable electrode assembly for placement on the epicardial surface of the heart, the electrode assembly comprising a distortable continuously extending resilient electric conductor forming an elongated oval shape in a first position and alternately forming a loop shape in a second position, the improvement comprising means enlarging the conductive area of said electrode assembly, said means comprising a plurality of flexible flat conductor strips positioned between spaced points on said electric conductor and conductively attached thereto.

* * * * *